United States Patent
Kim

(10) Patent No.: US 9,546,229 B2
(45) Date of Patent: Jan. 17, 2017

(54) COPOLYMERS CONTAINING PHOSPHORYLCHOLINE GROUPS AND METHODS OF PREPARING AND USING THE SAME

(71) Applicant: Hyungil Kim, Seoul (KR)

(72) Inventor: Hyungil Kim, Seoul (KR)

(73) Assignee: Suntech Co., Seoul (KR)

( * ) Notice: Subject to any disclaimer, the term of this patent is extended or adjusted under 35 U.S.C. 154(b) by 0 days.

(21) Appl. No.: 13/730,434

(22) Filed: Dec. 28, 2012

(65) Prior Publication Data

US 2013/0231400 A1    Sep. 5, 2013

(51) Int. Cl.
| | |
|---|---|
| *C08F 30/02* | (2006.01) |
| *C08F 2/38* | (2006.01) |
| *C08F 220/18* | (2006.01) |
| *C08F 230/02* | (2006.01) |

(52) U.S. Cl.
CPC ............. *C08F 30/02* (2013.01); *C08F 2/38* (2013.01); *C08F 220/18* (2013.01); *C08F 230/02* (2013.01)

(58) Field of Classification Search
USPC ....... 514/772.3, 506, 579; 526/210; 525/190
See application file for complete search history.

(56) References Cited

U.S. PATENT DOCUMENTS

| | | | | |
|---|---|---|---|---|
| 5,376,441 | A * | 12/1994 | Wu et al. | 428/304.4 |
| 6,204,324 | B1 | 3/2001 | Shuto et al. | |
| 6,214,957 | B1 | 4/2001 | Shiino et al. | |
| 7,230,063 | B1 | 6/2007 | Parker | |
| 7,714,075 | B1 | 5/2010 | Le et al. | |
| 2010/0069577 | A1 | 3/2010 | Couvreur et al. | |
| 2011/0178594 | A1 | 7/2011 | Kim et al. | |

FOREIGN PATENT DOCUMENTS

| | | |
|---|---|---|
| JP | H06313009 | 11/1994 |
| JP | 2005-239988 | 9/2005 |
| JP | 2010-513648 | 4/2010 |
| WO | 01/09208 | 2/2001 |

OTHER PUBLICATIONS

Ishihara, Kazuhiko et al. Preparation of Phospholipid Polymers and Their Properties as Polymer Hydrogel Membranes. Polymer Journal, 1990, vol. 22, No. 5, pp. 355-360.
Ueda, Tomoko et al. Peparation of 2-Methacryloyloxyethyl Phosphorylcholine Copolymers with Alkyl Methacrylates and Their Book Compatibility. Polymer Journal, 1992, vol. 24, No. 11, pp. 1259-1269.
Katakura, Osamu et al. Evaluation of 2-methacryloyloxyethyl phosphorylcholine (MPC) polymer-coated dressing on surgical wounds. J. Med Dent. Sci., 2005, 53:115-121.
Bhuchar, Neha et al. Detailed study of the reversible addition-fragmentation chain transfer polymerization and co-polymerization of 2-methacryloyloxyethyl phosphorylcholine. Polym. Chem., 2011, 2, 632-639.
Chen, Meng et al. Robust, Biomimetic Polymer Brush Layers Grown Directly from a Planar Mica Surface. ChemPhysChem, 2007, 8, 1303-1306.
Kim, Hyung Il et al. Tissue response to poly(L-lactic acid)-based blend with phospholipid polymer for biodegradable cardiovascular stents. Biomaterials, 2011, 32:2241-2247.
Yusa, Shin-ichi et al. Synthesis of Well-Defined Amphiphillic Block Copolymers Having Phospholipid Polymer Sequences as a Novel Biocompatible. Polymer Micelle Reagent. Biomacromolecules, 2005, 6:663-670.
European Search Report dated May 31, 2013 from European Patent Application No. 12199416.4, 4 Pages.
English Translation of Notification of Reasons for Rejection dated Apr. 1, 2014 from Japanese Patent Application No. 2013-040711, pp. 1-4.
Moad, Graeme et al. Living Radical Polymerization by the RAFT Process—A Third Update. Aust. J. Chem., 2012, vol. 65, pp. 985-1076.

* cited by examiner

*Primary Examiner* — Shobha Kantamneni
(74) *Attorney, Agent, or Firm* — MH2 Technology Law Group, LLP

(57) ABSTRACT

Methods for synthesizing a random copolymer having a phosphorylcholine group. Syntheses involving a reaction mixture containing a chain transfer agent (CTA), a solvent, a hydrophobic methacrylate monomer, a 2-methacryloyloxyethyl phosphorylcholine (MPC) monomer, and, optionally, an initiator. The random copolymers produced by such synthesis methods having a polydispersity index (PDI) of less than about 1.3 and a peak molecular weight ($M_p$) of less than about 130,000. Polymer blends and medical devices including such random copolymers, and methods of treating a mammal using such random copolymers or medical devices.

16 Claims, No Drawings

COPOLYMERS CONTAINING PHOSPHORYLCHOLINE GROUPS AND METHODS OF PREPARING AND USING THE SAME

CROSS-REFERENCE TO RELATED APPLICATIONS

This application claims priority to U.S. Provisional Patent Application 61/606,003 filed Mar. 2, 2012, the entire disclosure of which is hereby incorporated herein by reference in its entirety.

BACKGROUND

For polymers introduced into a living body it is desirable that they be non-toxic and that their biodistribution be predictable. It is also desirable that such polymers should have a controlled distribution of molecular weights and a controlled composition of repeating units, as well as being biocompatible. Phosphorylcholine groups are a major component of the outer membranes of eukaryotic cells, and polymers containing phosphorylcholine groups can enhance the biocompatibility of materials comprising the polymer.

U.S. Pat. No. 6,214,957 to Shiino et al., issued Apr. 10, 2001, and U.S. Pat. No. 6,204,324 to Shuto et al., issued Mar. 20, 2001, teach that solubilizers, emulsifiers, and dispersing agents moisturize the skin when used as washing agents and elevate the concentration of a material to be solubilized, emulsified, or dispersed in solvents including water. The water-soluble random copolymers containing phosphorylcholine groups taught by U.S. Pat. Nos. 6,214,957 and 6,204,324 are prepared by conventional free radical methods. The conventional free radical methods used in these issued patents do not permit control of the distribution of molecular weights and the composition of repeating units in copolymers produced. Polymers, like those taught by U.S. Pat. Nos. 6,214,957 and 6,204,324, prepared using conventional free radical synthesis methods, are not optimal for introduction into a mammalian (e.g., human) body.

In medicine, a stent is any device which is inserted into a blood vessel or other internal duct in order to expand the vessel to prevent or alleviate a blockage. Such devices have been fabricated from metal mesh and remain in the body permanently or until removed through further surgical intervention. A bioresorbable stent can serve the same purpose, but is manufactured from a resorbable or absorbable material.

Percutaneous transluminal coronary angioplasty (PTCA) is a common procedure for treating heart disease. A problem associated with PTCA is the formation of intimal flaps or torn arterial linings which can collapse and occlude the conduit after the balloon used in PTCA is deflated. Moreover, thrombosis and restenosis of the artery can develop over several months after the procedure, which can require another angioplasty procedure or a surgical by-pass operation. To reduce the partial or total occlusion of the artery by the collapse of arterial lining, and to reduce the chance of the development of thrombosis and restenosis, a stent can be introduced in the lumen to maintain the vascular patency.

Stents can be used not only as a mechanical intervention but also as a vehicle for providing biological therapy (e.g., delivery of at least one bioactive agent). As a mechanical intervention, stents act as scaffolds, functioning to physically hold open and, if desired, to expand the wall of a passageway (e.g., a blood vessel). Biological therapy can be achieved by medicating a stent. Medicated stents provide for the local administration of a therapeutic substance at a desired site. Local delivery can produce fewer side effects and can achieve more favorable results.

The use of metal drug-eluting stents can present some potential drawbacks. These include a predisposition to late stent thrombosis (the forming of blood clots long after the stent is in place), prevention of late vessel adaptive or expansive remodeling, hindrance of surgical revascularization, and impairment of imaging with multislice computed tomography (CT).

To overcome some of these potential drawbacks, bioresorbable or bioabsorbable stents are being developed. Like metal stents, placement of a bioresorbable stent will restore blood flow and support the vessel through the healing process. However, in the case of a bioresorbable stent, the stent will gradually resorb and be benignly cleared from the body, leaving no permanent implant.

Studies have shown that the most critical period of vessel healing is largely complete by approximately three months. Therefore, the goal of a bioresorbable or "temporary" stent is to fully support the vessel during this critical period, and then resorb from the body when it is no longer needed.

A coronary stent is a tube placed in the coronary arteries that supply the heart, to keep the arteries open in the treatment of coronary heart disease. Coronary stents reduce chest pain and have been shown to improve survivability in the event of an acute myocardial infarction.

Similar stents and procedures are used in non-coronary vessels, e.g., in the legs in treating peripheral artery disease. One of the drawbacks of vascular stents is the potential for restenosis via the development of a thick smooth muscle tissue inside the lumen, the so-called neointima. Development of a neointima is variable but can at times be so severe as to re-occlude the vessel lumen (restenosis), especially in the case of smaller diameter vessels, which often results in reintervention. Consequently, current research focuses on the reduction of neointima after stent placement.

A drug-eluting stent (DES) is a peripheral or coronary stent (a scaffold) placed into narrowed, diseased peripheral or coronary arteries that slowly releases a drug to block cell proliferation. This prevents fibrosis that, together with clots (thrombus), could otherwise block the stented artery.

A coating, typically of a polymer, holds and elutes (releases) the drug into the arterial wall by contact transfer in a drug-eluting stent. The first drug-eluting stents used durable coatings, but some newer coatings are designed to biodegrade after or as the drug is eluted. Coatings are typically spray coated or dip coated. There can be one to three or more layers in the coating, e.g., a base layer for adhesion, a main layer for holding the drug, and sometimes a top coat to slow down the release of the drug and extend its effect.

Stents can be fabricated from materials that are biocompatible and/or biodegradable. The goal is for the stent to have a biocompatible coating which demonstrates great safety with regard to stent thrombosis. The stent coatings can, in some instances, lower acute and sub-acute thrombosis rates. The coating material selected must not only have sufficient mechanical properties but also show excellent coating integrity. The preceding problem has been at least partially ameliorated by the use of increasingly biocompatible materials and/or biocompatible coatings.

It would be beneficial to have biocompatible polymers that form biomembrane-like structures to enhance biocompatibility and/or bioabsorbability. Providing polymeric medical devices which are resorbable/bioabsorbable upon introduction into a mammal and that comprise polymers that can be excreted (intact or as a degradation product) in the host's urine would be beneficial. Medical devices that include a polymer coating which reduces complications (e.g., stent thrombosis) would be desirable. Such polymers and medical devices would be particularly useful for coronary stents, although they would also provide substantial benefit to any manner of other medical devices introduced into a mammal. Such medical devices (i.e., drug-eluting stents, among others) should also demonstrate excellent mechanical properties.

SUMMARY

In embodiments, 2-methacryloyloxyethyl phosphorylcholine (MPC) and hydrophobic monomers (e.g., monomers that interact with hydrophobic substances) can be randomly polymerized into a polymer chain to produce a water-soluble zwitterionic random copolymer containing phosphorylcholine groups. Such polymers can have excellent flexibility in aqueous environments and good compatibility with other hydrophobic substances and can be synthesized by certain embodiments. Synthesized by a reversible addition-fragmentation chain transfer (RAFT) method, certain water-soluble zwitterionic random copolymers contain phosphorylcholine groups and can have a controlled distribution of molecular weights and a controlled composition of repeating units.

Certain embodiments are drawn to water-soluble random copolymers containing phosphorylcholine groups, which have relatively low polydispersity indices (PDIs) and relatively small molecular weights that can be introduced (e.g., injected, inserted or implanted) into a mammal (e.g., into a human blood vessel), and methods for synthesizing such copolymers.

Some embodiments are drawn to methods of synthesizing a copolymer comprising a phosphorylcholine group and having a polydispersity index (PDI) of less than about 1.3 and a peak molecular weight ($M_p$) of less than about 130,000. In certain aspects, the synthesis methods can comprise preparing a reaction mixture comprising (a) at least one chain transfer agent (CTA) comprising a thiocarbonylthio group, (b) a solvent comprising an alcohol, (c) at least one hydrophobic methacrylate monomer, (d) a 2-methacryloyloxyethyl phosphorylcholine (MPC) monomer, and, optionally, (e) an initiator.

In some embodiments, the molar ratio of the at least one hydrophobic methacrylate monomer to the MPC monomer in the reaction mixture can be between about 2.5:1 and about 1:4. The molar ratio of the total monomers (moles hydrophobic methacrylate monomer and moles of MPC monomer combined) to the CTA can be between about 35:1 and about 564:1, in certain aspects. In some embodiments, where an initiator is a component of the reaction mixture, the reaction mixture can comprise a mole ratio of CTA to initiator of between about 2.5:1 and about 10:1.

In some embodiments, the polymerization of the at least one hydrophobic methacrylate monomer and an MPC monomer can be carried out at a reaction temperature of 80° C. or above. Further, the at least one hydrophobic methacrylate monomer used in the synthesis methods can have the following formula (I):

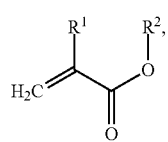

(I)

wherein $R^1$ is a hydrogen atom or a methyl group and $R^2$ is an alkyl group having 3 to 8 carbon atoms. In some embodiments, the hydrophobic methacrylate monomer can comprise n-butyl methacrylate (BMA) and/or 2-ethylhexyl methacrylate (EHMA).

In certain embodiments, the synthesis methods can comprise combining the at least one hydrophobic methacrylate monomer and a solvent (e.g., comprising alcohol) to produce a microemulsion before preparing the reaction mixture, and preparing the reaction mixture can comprise combining the microemulsion with a chain transfer agent (CTA), a 2-methacryloyloxyethyl phosphorylcholine (MPC) monomer, and, optionally, an initiator.

Some embodiments are drawn to copolymers comprising a random distribution of a phosphorylcholine repeating unit and at least one hydrophobic repeating unit. The copolymer can comprise:

(a) a phosphorylcholine repeating unit having the formula (II)

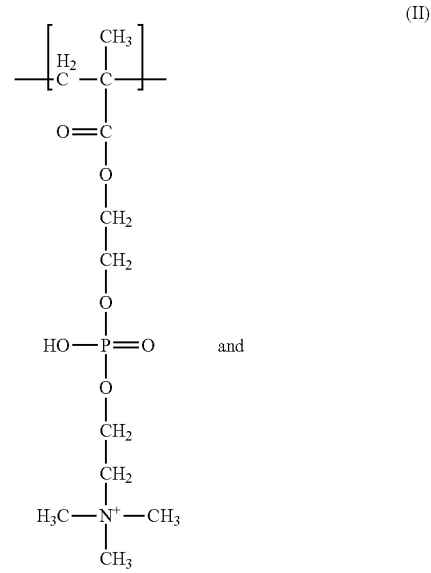

and (b) at least one hydrophobic repeating unit having the formula (III)

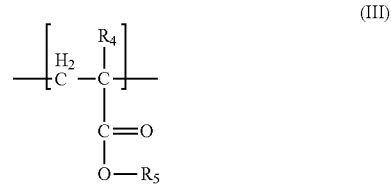

wherein $R^4$ is a hydrogen atom or a methyl group, $R^5$ is an alkyl group having 3 to 8 carbon atoms, and wherein the copolymer has a polydispersity index (PDI) of less than 1.3 and a peak molecular weight ($M_p$) of less than 130,000. The copolymer can comprise about 80 mol % or less of the phosphorylcholine repeating unit and about 20 mol % or more of the at least one hydrophobic repeating unit, in certain embodiments. In some embodiments, the copolymer is such that the copolymer's $M_p$ following its administration/injection to and urinary excretion by a rat is ±about 10% of its $M_p$ upon administration/injection to the rat. (See Examples below for guidance regarding how to measure $M_p$ of phosphorylcholine group-containing copolymers in the urine of Sprague Dawley rats following injection (administration) of the copolymer into the rats.)

Certain embodiments are drawn to polymer blends comprising at least one biocompatible polymer and a copolymer comprising a random distribution of a phosphorylcholine repeating unit and at least one hydrophobic repeating unit, as described above. The biocompatible polymer can comprise a lactic acid moiety (e.g., poly(L-lactic acid) (PLLA), poly(lactic-co-glycolic acid) (PLGA), poly(L-lactide-co-caprolactone) (PLCL), or a mixture thereof, among others), in some embodiments. A polymer blend can comprise between about 0.5 wt % and about 20 wt % of the copolymer comprising phosphorylcholine groups and between about 80 wt % and about 99.5 wt % of the biocompatible polymer, in certain embodiments. A polymer blend can further comprise a bioactive agent in some embodiments.

Certain embodiments are drawn to medical devices comprising a copolymer comprising phosphorylcholine groups or a polymer blend comprising both such a copolymer and at least one biocompatible polymer. In some embodiments, the medical device can be a vascular device (e.g., an artificial vessel, a stent, a vascular anastomotic device, a ventricular assist device, a hemopurification membrane, or a catheter, among others). The medical device can further comprise a bioactive agent.

Some embodiments are drawn to methods for treating a disorder in a mammal comprising introducing into the mammal a copolymer comprising a phosphorylcholine group or a medical device, as discussed above. The medical device can comprise a copolymer (comprising a phosphorylcholine repeating unit and a hydrophobic unit), as discussed above. Following introduction of the medical device into a mammal, at least some of copolymer is excreted in the mammal's urine.

DETAILED DESCRIPTION

The term "biodegradable" refers to materials selected to dissipate upon introduction within a body, independent of which mechanisms by which dissipation can occur, such as dissolution, degradation, absorption and excretion. The actual choice of which type of materials to use can readily be made by one of ordinary skill in the art. Such materials are often referred to by different terms in the art, such as "bioresorbable," "bioabsorbable," or "biodegradable", depending upon the mechanism by which the material dissipates. The prefix "bio" indicates that the erosion occurs under physiological conditions, as opposed to other erosion processes, caused for example, by high temperature, strong acids or bases, UV light or weather conditions.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause an undesirably adverse, long-lived or escalating biological reaction or response, and is distinguished from a mild, transient inflammation which typically accompanies surgery or introduction of foreign objects into a living organism.

As used herein, the phrase "introduced into a mammal" refers to an ability of a medical device to be positioned, partially or wholly, at a location on or within a body of a mammalian patient for any suitable period of time, such as within a blood vessel. In some embodiments, introduction into a mammal can involve implantation. Medical devices introduced into a mammal can be configured for transient placement within or on a body during a medical intervention (e.g., minutes to hours), or to remain in or on the body for a prolonged period of time after introduction (e.g., weeks or months or years). Medical devices can include devices configured for bioabsorption within a body during a prolonged period of time.

As used herein, the term "bioactive agent" can be any agent, which can be a therapeutic, prophylactic, ameliorative or diagnostic agent. The term "bioactive agent" can refer to any pharmaceutically active agent that produces an intended therapeutic effect on the body to treat or prevent a disease or a condition associated with a disease.

Synthesis Methods

Certain embodiments are drawn to methods of synthesizing a copolymer comprising a phosphorylcholine group. The copolymer synthesized by such methods can be a random copolymer, and in some embodiments the random copolymer can be zwitterionic.

Synthesis methods of certain embodiments rely on reversible addition-fragmentation chain transfer (RAFT). RAFT is a controlled free radical polymerization mediated by RAFT agents (e.g., chain transfer agents (CTAs)). These CTAs can be derived from specific dithioesters, xanthates, dithiocarbamates and trithiocarbonates and are selected to have both high chain transfer constants and good radical polymerization reinitiating efficiency. CTAs are discussed in greater detail below.

In some embodiments, the method can comprise: preparing a reaction mixture comprising at least one chain transfer agent (CTA) comprising a thiocarbonylthio group, a solvent comprising an alcohol, at least one hydrophobic methacrylate monomer, a 2-methacryloyloxyethyl phosphorylcholine (MPC) monomer, and, optionally, an initiator; and polymerizing the at least one hydrophobic methacrylate monomer and the MPC monomer at a reaction temperature of 80° C. or above, 90° C. or above, 120° C. or above, or 130° C. or above to form the copolymer. In some embodiments the reaction temperature for the polymerization step can be 80° C. or above. Certain embodiments can comprise combining the at least one hydrophobic methacrylate monomer and the solvent to produce a microemulsion before preparing the reaction mixture, and in these embodiments preparing the reaction mixture can comprise combining the microemulsion with the chain transfer agent (CTA), the 2-methacryloyloxyethyl phosphorylcholine (MPC) monomer, and, optionally, the initiator. The copolymer formed by such methods can have a polydispersity index (PDI) of less than about 1.3 and a peak molecular weight ($M_p$) of less than about 130,000, in some embodiments.

Methods, in certain embodiments, can comprise: combining at least one hydrophobic methacrylate monomer and a solvent to produce a microemulsion; preparing a reaction mixture comprising a chain transfer agent (CTA) comprising a thiocarbonylthio group, the microemulsion and a 2-methacryloyloxyethyl phosphorylcholine (MPC) monomer, and, optionally, an initiator; and polymerizing the at least one hydrophobic methacrylate monomer and the MPC monomer to form the random copolymer. The copolymer formed by such methods can, in some embodiments, have a polydispersity index (PDI) of less than about 1.3 and a peak molecular weight ($M_p$) of less than about 130,000. In some embodiments, the polymerizing of the at least one hydrophobic methacrylate monomer and the MPC monomer can be carried out at a reaction temperature of 80° C. or above, 90° C. or above, 120° C. or above, or 130° C. or above to form the copolymer. In some embodiments the reaction temperature for the polymerization step can be 80° C. or above. The micelles droplets in the microemulsion of the at least one hydrophobic methacrylate monomer and the solvent can have a droplet size of less than about 0.5 μm or less than about 0.2 μm In certain embodiments, the methods can comprise using (a) an alcohol as a solvent, (b) at least one hydrophobic methacrylate monomer which forms a microemulsion having droplets more than 10 nm in diameter in the alcohol or alcohol solution, (c) 2-methacryloyloxyethyl phosphorylcholine (MPC) monomer, (d) a chain transfer agent, (e) an initiator, and (f) a reaction temperature of about 80° C. or more, 90° C. or above, 120° C. or above, or 130° C. or above, and the methods can provide water-soluble zwitterionic random copolymers comprising (a) a phosphorylcholine repeating unit at a mole fraction of about 80% or less, (b) a non-ionic and hydrophobic repeating unit at a mole fraction of about 20% or more, (c) a polydispersity index (PDI) less than about 1.3, and (d) a peak molecular weight ($M_p$) of less than about 130,000.

In some embodiments, the polymerizing step can be performed for from about 4 hours to about 48 hours, from about 6 hours to about 48 hours, or from about 18 hours to about 48 hours.

Hydrophobic Methacrylate Monomers

In some embodiments the hydrophobic methacrylate monomer used in the synthesis methods discussed above can comprise N,N-dimethylaminoethyl methacrylate, N,N-diethylaminoethyl methacrylate, and quaternary salts thereof; 2,2-hydroxyethyl methacrylate; methacrylic acid monoglycerol; polyethylene glycol methacrylate; butyl methacrylate (BMA); propyl methacrylate; hexyl methacrylate; cyclohexyl methacrylate; allyl methacrylate; benzyl methacrylate; decyl methacrylate; isdecyl methacrylate; dodecyl methacrylate; cetyl methacrylate; stearyl methacrylate; cyclohexyl methacrylate; 2-ethylhexyl methacrylate (EHMA); glycidyl methacrylate; methacryloyloxyethyl trimethoxysilane; 2-methacryloyloxyethyl butyl urethane; 2-methacryloyloxyethyl benzyl urethane; or 2-(meth)acryloyloxyethyl phenyl urethane.

The at least one hydrophobic methacrylate monomer used in certain embodiments can have the following formula (I):

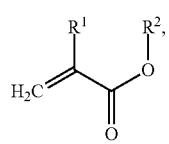

(I)

wherein $R^1$ is a hydrogen atom or a methyl group and $R^2$ is an alkyl group having 3 to 8 carbon atoms.

In some embodiments the at least one hydrophobic methacrylate monomer can comprise n-butyl methacrylate (BMA) and/or 2-ethylhexyl methacrylate (EHMA).

2-Methacryloyloxyethyl Phosphorylcholine (MPC) Monomer and Monomer Proportions

2-Methacryloyloxyethyl phosphorylcholine (MPC) monomer has the following formula:

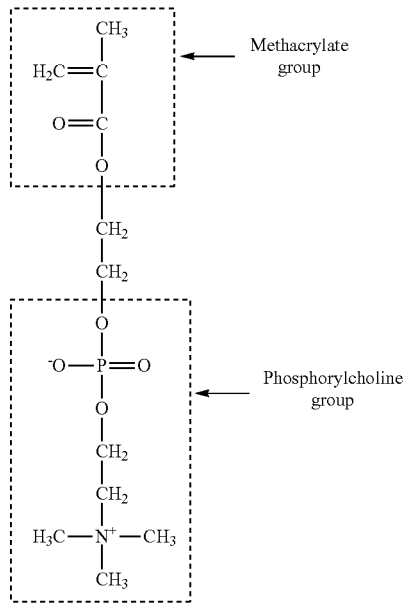

The methacrylate group of the MPC monomer can be incorporated into the copolymer backbone and the phosphorylcholine group can become a moiety pendant to the copolymer backbone. The copolymer can comprise about 20 mol % to about 80 mol % of the phosphorylcholine group-containing repeating unit (formula (II) below); or from about 30 mol % to about 50 mol % of the phosphorylcholine group-containing repeating unit, in some embodiments.

Following polymerization, the copolymer produced can have a repeating unit derived from the MPC monomer and having the formula (II)

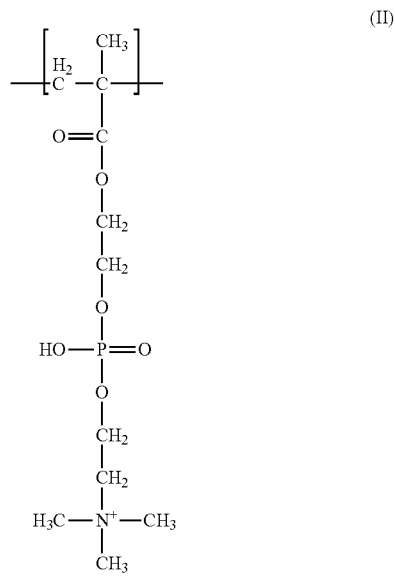

(II)

In some embodiments the molar ratio of the at least one hydrophobic methacrylate monomer to the MPC monomer in the polymerization reaction mixture can be between about 2.5:1 and about 1:4; between about 2.3:1 to about 1:4; or between about 1:1 to about 1:4.

Solvents and Microemulsions

The solvent used in the reaction mixture can comprise at least one alcohol. In some embodiments, the alcohol contained in the solvent can have the formula $R^3$—OH, wherein $R^3$ is an alkyl group having 1 to 4 carbon atoms. The solvent can comprise methanol, ethanol, propanol, isopropanol, butanol, isobutanol, tertbutanol, or mixtures thereof, in certain embodiments. In some aspects, the solvent can comprise methanol, ethanol, butanol, or a mixture of two or more thereof. In certain embodiments, the solvent can comprise up to about 30 wt %, up to about 20 wt %, up to about 15 wt %, or up to about 10 wt % water in addition to other components (e.g., the alcohol).

In some embodiments, the solvent and the hydrophobic methacrylate monomer can form a microemulsion. The solvent can be any known in the art that will form a microemulsion with the hydrophobic methacrylate monomer.

Alcohols can be good solvents for the MPC monomer, chain transfer agents, and initiators. Some hydrophobic methacrylate monomers can form a microemulsion in alcohol. When a hydrophobic methacrylate monomer and a solvent (e.g., comprising alcohol) are mixed, the mixture can, in some embodiments, form monomer-swollen micelles (diameter, 10 nm~10 μm) dispersed in alcohol and large droplets of hydrophobic monomer can be stabilized by the MPC monomer. Table 1-1 shows the droplet size of hydrophobic methacrylate monomers stabilized by the MPC monomer in alcohols as determined by a dynamic light scattering.

TABLE 1-1

Microemulsions of methacrylate monomers in alcohols

| Hydrophobic Methacrylate Monomer | Alcohol | Droplet Size (nm) |
|---|---|---|
| n-butyl methacrylate (BMA) | MeOH | 200~1000 |
| n-butyl methacrylate (BMA) | EtOH | 50~500 |
| n-butyl methacrylate (BMA) | BuOH | 10~200 |
| 2-ethylhexyl methacrylate (EHMA) | MeOH | 300~1000 |
| 2-ethylhexyl methacrylate (EHMA) | EtOH | 50~500 |
| 2-ethylhexyl methacrylate (EHMA) | BuOH | 20~200 |
| Ethyl methacrylate (EMA) | EtOH | 100~500 |
| Lauryl methacrylate (LMA) | BuOH | 200~10000 |

In some embodiments, the microemulsion can comprise methanol and butyl methacrylate or the microemulsion can comprise ethanol and 2-ethylhexyl methacrylate (EHMA).

Chain Transfer Agents (CTAs)

RAFT or Reversible Addition-Fragmentation chain Transfer is a form of living radical polymerization. The present methods, discussed above, can be carried out using RAFT polymerization. Chain transfer agents (CTAs) are also referred to as Reversible Addition-Fragmentation chain Transfer agents (RAFT agents) in the art. CTAs mediate the polymerization in methods discussed above via a reversible-chain transfer process. In some embodiments, a CTA can have both a chain transfer activity and a polymerization initiation activity. The chain transfer agent used in embodiments can be selected from those in the art.

For example, the CTA can comprise a dithioester (including both aromatic and aliphatic dithioesters), a dithiocarbamate, a trithiocarbonate, a xanthate, or a mixture of two or more thereof. In certain embodiments, the CTA can comprise a thiocarbonylthio group. In some embodiments, the CTA can comprise 4-cyano-4-[(dodecylsulfanylthiocarbonyl)sulfanyl]pentanoic acid (CTTC), 4-Cyanopentanoic acid dithiobenzoate (CDTB), 2-cyano-2-propyl benzodithioate, 2-cyano-2-propyl dodecyl trithiocarbonate, or a mixture of two or more thereof. $R^1$ can be a methyl group in the hydrophobic methacrylate monomer of Formula (I) and the CTA can comprise 4-cyano-4-[(dodecylsulfanylthiocarbonyl)sulfanyl]pentanoic acid (CTTC), 4-Cyanopentanoic acid dithiobenzoate (CDTB), 2-cyano-2-propyl benzodithioate, 2-cyano-2-propyl dodecyl trithiocarbonate, or a mixture of two or more thereof, in some embodiments.

In certain embodiments, the CTA can comprise cyanomethyl dodecyl trithiocarbonate, 2-(dodecylthiocarbonothioylthio)-2-methylpropionic acid or a mixture thereof. $R^1$ can be H in the hydrophobic methacrylate monomer of Formula (I) and the CTA can comprise cyanomethyl dodecyl trithiocarbonate, 2-(dodecylthiocarbonothioylthio)-2-methylpropionic acid, or a mixture thereof, in some embodiments.

In some embodiments, the molar ratio of the total monomers (moles of the at least one hydrophobic methacrylate monomer and moles of MPC monomer combined) to the CTA in the reaction mixture used to produced the copolymer can be between about 35:1 and about 564:1; about 35:1 and about 141:1; or about 35:1 and about 70:1.

Optional Initiator

A polymerization initiator can be selected from those known in the art. The choice of initiator can depend on: a) its solubility and b) its decomposition temperature. Thus, when the polymerization is performed in an organic solvent (e.g., an alcohol), the initiator can be selected to be soluble in that solvent and the decomposition temperature of the initiator can be at or below the boiling point of the solvent. The initiator can be used as a radical source for the polymerization reaction. Thus, the initiator is first relied on to create radicals, which can, in turn, be transferred from the initiator molecule to a monomer unit present in the reaction mixture. As discussed above, it is known in the art that some CTAs can also act as initiators. If a CTA has both chain transfer activity and initiator activity, then an initiator may not be necessary to proceed with polymerization. However, in some embodiments the reaction mixture can comprise both a CTA (e.g., a CTA having only chain transfer activity or a CTA having both chain transfer activity and initiator activity) and an initiator.

In some embodiments, the reaction mixture can comprise an initiator. In certain embodiments the initiator can comprise 2,2'-azobis(2-amidinopropane)dihydrochloride, 4,4'-azobis(4-cyanovaleric acid) (ACVA), 2,2'-azobis(2-(5-methyl-2-imidazo line-2-yl)propane)dihydrochloride, 2,2'-azobis(2-(2-imidazoline-2-yl)propane)dihydrochloride, 2,2'-azobisisobutylamide dihydrate, ammonium persulfate, potassium persulfate, benzoyl peroxide, diisopropyl peroxy dicarbonate, t-butylperoxy-2-ethylhexanoate, t-butyl peroxypivalate, t-butylperoxydiisobutylate, lauroyl peroxide, azobisisobutyronitrile (AIBN), 2,2'-azobis(2,4-dimethylvaleronitrile), t-butyl peroxyneodecanoate, 2,2'-azobis(2-methylpropionamidine)dihydrochloride (AAPH), 1,1'-azobis(cyclohexanecarbonitrile) (ACHN), or a mixture of two or more thereof.

In some embodiments, the reaction mixture can comprise azobisisobutyronitrile (AIBN) and/or 4,4'-azobis(4-cyanovaleric acid) (ACVA) as an initiator.

In certain embodiments, the reaction mixture can comprise an initiator and the mole ratio of CTA to the initiator can be between about 2.5:1 and about 10:1; between about 4.5:1 and about 10:1; or between about 5:1 and about 10:1.

Copolymers

Certain embodiments are drawn to copolymers comprising a random distribution of a phosphorylcholine repeating unit and at least one hydrophobic repeating unit. The copolymer can be a random copolymer and in some embodiments, the copolymer can be zwitterionic. The copolymer can be prepared using synthesis methods discussed above.

In embodiments, the copolymer can comprise:
(a) a phosphorylcholine repeating unit having the formula (II)

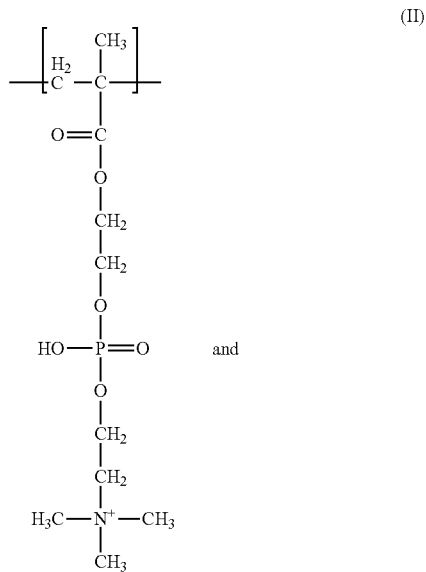

(b) at least one hydrophobic repeating unit having the formula (III)

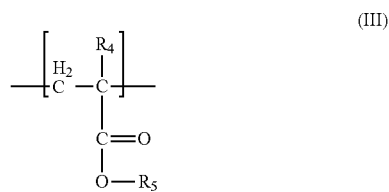

wherein $R^4$ is a hydrogen atom or a methyl group, $R^5$ is an alkyl group having 3 to 8 carbon atoms, and wherein the copolymer has a polydispersity index (PDI) of less than 1.3 and a peak molecular weight ($M_p$) of less than 130,000.

In some embodiments, the copolymer can be soluble in an aqueous solution. $R^4$ can be a methyl group in certain copolymers. In certain embodiments, $R^5$ can be a butyl group or a 2-ethylhexyl group. $R^4$ can be a methyl group and $R^5$ can be a butyl group or a 2-ethylhexyl group in some embodiments.

Number average molecular weight ($M_n$) is the statistical average molecular weight of all the polymer chains in a sample. Weight average molecular weight ($M_w$) compared to $M_n$ takes into account the molecular weight of a chain in determining contributions to the molecular weight average. The more massive the chain, the more the chain contributes to $M_w$. $M_w$ can be determined by methods that are sensitive to molecular size rather than just their number. Peak molecular weight ($M_p$) is the molecular weight at the highest peak (e.g., the mode) of a molecular weight distribution for a polymer sample.

The peak molecular weight ($M_p$) of copolymers of certain embodiments can be less than about 130,000; less than about 120,000; less than about 100,000; less than about 95,000; less than about 70,000; or less than about 60,000.

The polydispersity index (PDI) or heterogeneity index of a polymer can be used to characterize polymers having a range of molecular weights as opposed to a single molecular weight. The PDI represents the breadth of the molecular weight distribution of a polymer in a sample. PDI, as used herein, refers to the ratio of the weight-average and number-average molecular weights ($M_w/M_n$). As polymer chains in a sample approach a uniform chain length, the PDI approaches 1. The larger the PDI the broader the range of molecular weights in a sample.

The polydispersity of a compound (e.g., polymer), as well as its $M_p$, can be determined using methods known in the art. For example the PDI and $M_p$ can be determined using gel permeation chromatography (also referred to as "size exclusion chromatography"), light scattering measurements (e.g., dynamic light scattering), or direct calculation from matrix-assisted laser desorption/ionization (MALDI) or electrospray mass spectrometry (ES-MS), among others. In some embodiments, the copolymer can have PDI of less than about 1.2; less than about 1.19; less than about 1.18; or less than about 1.16. In one embodiment, the PDI and $M_p$ are measured using gel permeation chromatography, where the polymer is dissolved in 1,1,1,3,3,3-hexafluoroisopropanol (HFIP) with 10 mM sodium trifluoroacetate, a sample of the dissolved polymer (35 µl injection volume) is loaded onto 2 Agilent PL HFIP gel columns (250×4.6 mm) at 40° C. and eluted from the columns with HFIP with 10 mM sodium trifluoroacetate at a flow rate of 0.2 mL/min, and compared to poly[n-butyl methacrylate (BMA)] standard samples having a molecular weight range from 1,500 to 800,000 that are dissolved in HFIP with 10 mM sodium trifluoroacetate and run through the 2 Agilent PL HFIP gel columns (250×4.6 mm) under the same conditions as the polymers.

In some embodiments, the copolymer can be administered to/introduced into a mammal and at least some of the copolymer (and/or degradation products thereof) can be excreted in the mammal's urine. Following excretion from a rat (such as a Sprague Dawley rat) injected with a phosphorylcholine group-containing copolymer, the PDI of the copolymer remains substantially unchanged as compared to the PDI of the copolymer upon administration to the rat. For example, the copolymer excreted in the urine can have a PDI that is ±about 10% of the PDI of the copolymer upon its injection into (administration to) the rat. In certain embodiments, the copolymer excreted in the urine can have a PDI that is ±about 10%, ±about 8%, ±about 5%, or ±about 2.5% of the PDI of the copolymer upon its injection (administration). Similarly, flowing excretion from the urine, the $M_p$ of the copolymer remains substantially unchanged as compared to the $M_p$ of the copolymer upon administration to the rat. For example, the copolymer excreted in the urine can have a peak molecular weight ($M_p$) that is ±about 15%, ±about 10%, ±about 8%, ±about 5%, ±about 4.5%, or ±about 2.5% of the $M_p$ of the copolymer upon its injection (administration). (See Examples below for guidance regarding how to measure PDI or $M_p$ of phosphorylcholine group-containing copolymers in the urine of Sprague Dawley rats following injection (administration) of the copolymer into the rats.) A phosphorylcholine-containing copolymer, as discussed above, can be excreted in a rat's urine from 2 hours to 48 hours after being administered to the rat and most (>detection sensitivity) of 100 mg of the phosphorylcholine group-containing copolymer introduced into a rat can be excreted within 24 hours of its administration.

In certain embodiments, the copolymer can comprise about 80 mol % or less of the phosphorylcholine repeating unit having formula (II) and about 20 mol % or more of the hydrophobic repeating unit having formula (III). In some embodiments, the copolymer can comprise about 20 mol % to about 80 mol % of the phosphorylcholine repeating unit; or about 30 mol % to about 50 mol % of the phosphorylcholine repeating unit.

Purification of the copolymer can be performed in accordance with general purification methods such as reprecipitation, dialysis, and ultrafiltration, in some embodiments.

Polymer Blends

Some embodiments are drawn to polymer blends comprising at least one biocompatible polymer and a copolymer containing phosphorylcholine groups, as discussed above. The biocompatible polymer can also be bioabsorable in certain embodiments. Suitable biocompatible polymers can comprise poly(lactic acid) (PLA), poly(L-lactic acid), poly (D,L-lactic acid), polyglycolic acid (PGA), poly(D-lactic-co-glycolic acid), poly(L-lactic-co-glycolic acid), poly(D,L-lactic-co-glycolic acid), poly($\epsilon$-caprolactone), poly (valerolactone), poly(hydroxybutyrate), polydioxanone, poly(hydroxyl butyrate), and poly(hydrovalerate), among others. The biocompatible polymers can comprise polyglactin (a co-polymer of lactic acid and glycolic acid (PGA-PLA)), polyglyconate (a co-polymer of trimethylene cargonate and glycolide), a co-polymer of polyglycolic acid and $\epsilon$-caprolactone, a co-polymer of poly(lactic acid) and $\epsilon$-caprolactone, poly(lactic acid)-poly(ethylene glycol) block co-polymer, and poly(ethylene oxide)-poly(butyleneteraphthalate), poly(lactic acid-co-trimethylene carbonate), poly($\epsilon$-caprolactone copolymer), and poly(L-lactic acid copolymers), among others.

The biocompatible polymer can comprise a lactic acid moiety in embodiments. In some aspects, the biocompatible polymer can comprise a biodegradable polymer comprising a polylactide (PLA), a polyglycolide (PGA), a poly(lactide-co-glycolide (PLGA), a polyanhydride, a polyorthoester, or a mixture thereof. In certain embodiments, the biocompatible polymer can comprise poly(L-lactic acid) (PLLA), poly(lactic-co-glycolic acid) (PLGA), poly(L-lactide-co-caprolactone)(PLCL), or a mixture of two or more thereof.

Blending of the at least one biocompatible polymer and the copolymer containing phosphorylcholine groups, can be performed by mechanical blending, solvent casting or latex blending, among other methods known in the art. Mechanical blending is a method of blending amorphous polymer materials above $T_g$ or blending crystalline polymer materials at $T_m$ or more. Solvent casting is a method of dissolving polymer materials in solvents followed by the removal of the solvents from the product. Latex blending is a method of blending polymer materials finely distributed in a liquid rubber (latex) to aggregate the blended polymer materials in latex. Solvent casting enables homogeneous distribution of copolymer comprising a phosphorylcholine group in a biocompatible polymer (i.e., PLLA, among others) and can improve the mechanical strength of a biocompatible polymer and can provide a phosphorylcholine group-rich surface, in some embodiments. Polymer blends of certain embodiments can have higher breaking strengths than the biocompatible polymer (i.e., PLLA, among others) by itself. See the Examples below.

In embodiments, the polymer blend can comprise between about 0.5 wt % and about 30 wt % of the copolymer containing phosphorylcholine groups (as discussed above) and between about 70 wt % and about 99.5 wt % of the biocompatible polymer; or between about 1 wt % and about 10 wt % of the copolymer containing phosphorylcholine groups and between about 90 wt % and about 99 wt % of the biocompatible polymer.

In some embodiments the polymer blend, comprises a copolymer comprising repeating units having formulas (II) and (III) (discussed above), $R^4$ is a methyl group and $R^5$ is a butyl group and the biocompatible polymer comprises poly(L-lactic acid) (PLLA) and/or poly(L-lactide-co-caprolactone)(PLCL).

A polymer blend can comprise at least one bioactive agent, in addition to the biocompatible polymer and the phosphorylcholine group-containing copolymer, in some embodiments. Bioactive agents can have anti-proliferative or anti-inflammatory properties or can have other properties such as antineoplastic, antiplatelet, anti-coagulant, anti-fibrin, antithrombonic, antimitotic, antibiotic, antiallergic, and antioxidant activities, among others. Examples of bioactive agents include: synthetic inorganic and organic compounds, proteins and peptides, polysaccharides and other sugars, lipids, and DNA and RNA nucleic acid sequences having therapeutic, prophylactic or diagnostic activities, among others. Nucleic acid sequences include genes and antisense molecules which bind to complementary DNA to inhibit transcription and ribozymes.

Some other examples of bioactive agents include: antibodies, receptor ligands, enzymes, adhesion peptides, blood clotting factors, inhibitors or clot dissolving agents (such as streptokinase), tissue plasminogen activator, antigens for immunization, hormones and growth factors, and oligonucleotides (such as antisense oligonucleotides and ribozymes and retroviral vectors for use in gene therapy), among others. The bioactive agent can comprise an immunosuppressant, an anti-inflammatory drug, an antimicrobial, an antiplatelet drug, an antiproliferative drug, or a combination of two or more thereof.

The immunosuppressant can be selected from those known in the art. In some embodiments the immunosuppressant can be a "limus" drug. Examples of limus drugs include: zotarolimus, umirolimus (e.g., biolimus), everolimus, pimecrolimus, and sirolimus (e.g., rapamycin), among others.

The foregoing substances can also be used in the form of prodrugs or co-drugs thereof as bioactive agents. The foregoing substances are listed by way of examples of bioactive agents and are not meant to be limiting. Other bioactive agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the mammal; the nature of the trauma; the nature of the therapy desired; the time over which the ingredient introduced resides at the introduction site; and whether other active agents are employed, the nature and type of the substance or combination of substances.

In certain embodiments, the blend can comprise a component that renders the polymer blend radiopaque.

Medical Devices

Certain embodiments are drawn to medical devices comprising a copolymer containing phosphorylcholine groups, as discussed above. In some embodiments, a medical device comprises a blend, as discussed above, comprising at least one biocompatible polymer and a copolymer having phosphorylcholine groups.

In embodiments the medical device can be an appliance that is totally or partly introduced (surgically or medically) into a mammal's body or by medical intervention into a natural orifice, and which is intended to remain there after the procedure. The duration of introduction (e.g., implantation) can be essentially permanent, i.e., intended to remain in place for the remaining lifespan of the patient; until the device biodegrades; or until it is physically removed.

Examples of medical devices include, without limitation, cardiac pacemakers and defibrillators, leads and electrodes for the preceding, organ stimulators such as nerve, bladder, sphincter and diaphragm stimulators, cochlear implants, prostheses, vascular grafts, self-expandable stents, balloon-expandable stents, stent-grafts, grafts, PFO closure devices, arterial closure devices, artificial heart valves and cerebrospinal fluid shunts. Examples of such medical devices include: self-expandable stents, balloon-expandable stents, stent-grafts, grafts (e.g., aortic grafts), artificial heart valves, cerebrospinal fluid shunts, pacemaker electrodes, and endocardial leads. In embodiments, the medical device can be a vascular device. In some embodiments, the medical device can be an artificial vessel, a stent, a vascular anastomotic device, a ventricular assist device, a hemopurification membrane, or a catheter. The underlying structure of the device can be any design known in the art. In embodiments, the medical device can be a stent (e.g., a soluble stent, a metal stent coated with a copolymer comprising a phosphorylcholine group, or a bare polymer-based stent).

A stent refers generally to any device used to hold tissue in place in a patient's (mammal's) body. Particularly useful stents are those used for the maintenance of the patency of a vessel in a patient's body when the vessel is narrowed or closed due to diseases or disorders including, without limitation, tumors (in, for example, bile ducts, the esophagus or the trachea/bronchi), benign pancreatic disease, coronary artery disease, carotid artery disease, renal artery disease and peripheral arterial disease such as atherosclerosis, restenosis and a vulnerable plaque.

For example, a stent can be used to strengthen the wall of the vessel in the vicinity of a vulnerable plaque (VP). VP refers to a fatty build-up in an artery thought to be caused by inflammation. The VP is covered by a thin fibrous cap that can rupture leading to blood clot formation. Thus, a stent can not only maintain vessel patency but can act as a shield against VP rupture.

A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction, among others.

Medical devices can also be employed for the localized delivery of therapeutic agents to specific treatment sites in a patient's body. Indeed, therapeutic agent delivery can be the sole purpose of the medical device or the medical device (i.e., stent) can be primarily intended for another use such as those discussed above with drug delivery providing an ancillary benefit. Certain embodiments are drawn to drug delivery systems/reservoirs. For example, contact lenses or intraocular lenses can be used to elute a drug to treat the eye.

The medical device can, in some embodiments, contain a metallic material or an alloy such as, but not limited to, cobalt chromium alloy, stainless steel, high nitrogen stainless steel, cobalt chrome alloy, tantalum, nickel-titanium alloy, platinum-iridium alloy, gold, magnesium, or combinations thereof, in addition to a copolymer comprising a phosphorylcholine group. Exemplary metal stent materials include, without limitation, stainless steel, nitinol, tantalum, tantalum alloy, titanium, titanium alloy, cobalt chromium, nickel chromium iron alloy, niobium, niobium alloy, zirconium and zirconium alloy. Exemplary bare polymer stent materials and soluble stent materials are known to those skilled in the art. Medical devices can comprise bioabsorbable and/or biocompatible polymers, in addition to a copolymer comprising a phosphorylcholine group or a polymer blend comprising the same. The medical device itself, such as a stent, can also be made from the described inventive polymers or polymer blends. It will be appreciated that biodegradable stents can be made from single polymers or co-polymers (for example, a co-polymer of L-lactide and ε-caprolactone as described in U.S. Pat. No. 5,670,161 or a terpolymer of L-lactide, glycolide and ε-caprolactone as described in U.S. Pat. No. 5,085,629 in addition to a copolymer comprising phosphorylcholine groups as discussed above.

In embodiments the medical device can comprise a coating containing a bioactive agent and a copolymer comprising phosphorylcholine groups or polymer blends containing such a copolymer, and the coating can become soluble in vivo, thereby allowing for sustained release of the bioactive agent and efficient biodegradation of the coating. A medical device coating can comprise a bioelastomer, PLGA, PLA, PEG, Zein (a protein extract obtained form corn), or a hydrogel, among others. In certain embodiments, the coating can comprise microcrystalline cellulose, hydroxypropylmethyl cellulose, hydroxypropyl cellulose, a cellulose product, a cellulose derivative, a polysaccharide or a polysaccharide derivative, among others. In some embodiments, the coating can include: lactose, dextrose, mannitol, a derivative of lactose, dextrose, mannitol, starch or a starch derivative, among others. A coating can be applied using methods known in the art (i.e., spray coating, dip coating, and immersion, among others).

If the medical device is a stent used for patency maintenance it can be delivered to the target site in a compressed state and then expanded to fit the vessel into which it has been inserted. Once at a target location, a stent can be self-expandable or balloon expandable. Due to the expansion of the stent, however, the stent coating can be flexible and capable of elongation, in some embodiments.

In certain embodiments, the medical devices can further comprise a bioactive agent, as discussed above. The bioactive agent can be a component of a polymer blend that is a component of the medical device. The bioactive agents can comprise an immunosuppressant, an anti-inflammatory drug, an antimicrobial, an antiplatelet drug, an antiproliferative drug, or a combination of two or more thereof. In some embodiments, the medical devices can comprise a substrate (i.e., a metal or polymer stent material) and a coating on at least one surface of the substrate, and the coating can comprise a copolymer comprising phosphorylcholine groups or a polymer blend comprising such a copolymer. The coating can comprise a bioactive agent.

In some embodiments, where the structure of the medical device is composed of a radiolucent material, a conventional radiopaque coating can be applied to it. For example, where the medical device is a vascular stent, the coating can provide a means for identifying the location of the stent by X-ray or fluoroscopy during or after its introduction into the patient's vascular system.

The medical device can further include a non-toxic radiopaque marker, such as, for example, barium sulfate or bismuth trioxide, in a copolymer or polymer blend prior to medical device formation to increase the radiopacity of the stents. The medical device can be coated with one or more radiopaque layers of non-ionic, water-soluble, iodinated contrast medium having a molecular weight of approximately 1 milligram (+/−20%) and a thickness of about 0.5 to 5 microns. In an embodiment, the radiopaque coating can be thin and temporary as by bioabsorption. The iodinated contrast can be water-soluble for faster absorption by body tissue. The contrast media can also have a low osmolality to reduce tonicity, chemical toxicity, hypersensitivity, and other potentially adverse side effects. It will be appreciated that a combination of contrast agents can be used in the same layer or in separate layers. It will further be appreciated that one or more contrast agents can be included in a polymer used in the medical device and one or more different or same contrast agents can be coated on the medical device. Alternatively, the contrast media can be hydrophobic. Hydrophobic contrast media can be utilized in applications that require slower rates of degradation or excretion.

Methods of Treatment

Certain embodiments are drawn to methods of treating a disorder in a mammal. The methods of treatment can comprise introducing into a mammal a copolymer comprising phosphorylcholine groups, as discussed above, or a medical device that comprises the copolymer comprising phosphorylcholine groups as discussed above, where following introduction at least some of copolymer is excreted in the mammal's urine.

In some embodiments, methods of treating a disorder can comprise introducing a stent (as a medical device) into a mammal, wherein the stent comprises a copolymer comprising phosphorylcholine groups, as discussed above, or a polymer blend comprising such a copolymer.

In certain embodiments, methods of treatment comprise treating atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, or a combination of two or more thereof.

Medical devices introduced into a mammal, in some embodiments, can further comprise a bioactive agent. In some embodiments, the bioactive agent can comprise an immunosuppressant, an anti-inflammatory drug, an antimicrobial, an antiplatelet drug, an antiproliferative drug, or a combination of two or more thereof.

In certain embodiments, the medical device can be prepared by casting the polymer blend comprising a copolymer comprising phosphorylcholine groups. The medical device can comprise a drug reservoir containing at least one drug and upon introduction into the mammal the drug can be released locally. In some embodiments, the medical device can be a drug delivery system for local delivery of drugs. For example, the medical device can, in some embodiments, release chemotherapy drugs to a tumor after its introduction into a mammal.

In accordance with embodiments, a coating comprising a copolymer comprising phosphorylcholine groups can be formed on a medical device (e.g., a stent) or the medical device itself can be made of a polymer blend comprising a copolymer containing phosphorylcholine groups. For coatings including one or more bioactive agents, the bioagent can be retained by the medical device (such as a stent) during delivery and expansion of the device, and released at a desired rate and for a predetermined duration of time at the site of introduction.

In accordance with some other embodiments, bioabsorbable or non-degradable devices can be formed of a material containing the copolymer comprising phosphorylcholine groups prepared using methods discussed above. The material can be the copolymer containing phosphorylcholine groups or a polymer blend such a polymer with one or more biocompatible polymers, optionally with a bioactive agent, which are defined above. The medical device can be a stent. A stent having the above-described coating can be useful for a variety of medical procedures, including, by way of example, treatment of obstructions caused by tumors in bile ducts, esophagus, trachea/bronchi and other biological passageways. A stent having the above-described coating can be useful for treating occluded regions of blood vessels caused by abnormal or inappropriate migration and proliferation of smooth muscle cells, thrombosis, and restenosis, among others. Stents can be placed in a wide array of blood vessels, both arteries and veins. Representative examples of sites include the iliac, renal, and coronary arteries, among others.

The following Examples further define and describe embodiments herein. Unless otherwise indicated, all parts and percentages are by weight.

EXAMPLES

Characterization of Microemulsion

A mixture of a hydrophobic methacrylate monomer and an alcohol (both specified in Table 1-1, below) formed monomer-swollen micelles (diameter, 10 nm~10 μm) dispersed in alcohol. Large droplets of the hydrophobic monomer were stabilized by the MPC monomer. Table 1-1 shows the droplet size of hydrophobic methacrylate monomers stabilized by the MPC monomer in alcohols. The diameters of the droplets were determined by dynamic light scattering.

TABLE 1-1

Microemulsion of methacrylate monomers in alcohols

| Hydrophobic Methacrylate Monomer | Alcohol | Droplet Size (nm) |
|---|---|---|
| n-butyl methacrylate (BMA) | MeOH | 200~1000 |
| n-butyl methacrylate (BMA) | EtOH | 50~500 |
| n-butyl methacrylate (BMA) | BuOH | 10~200 |
| 2-ethylhexyl methacrylate (EHMA) | MeOH | 300~1000 |
| 2-ethylhexyl methacrylate (EHMA) | EtOH | 50~500 |
| 2-ethylhexyl methacrylate (EHMA) | BuOH | 20~200 |
| Ethyl methacrylate (EMA) | EtOH | 100~500 |
| Lauryl methacrylate (LMA) | BuOH | 200~10000 |

Synthesis of Copolymer Samples 1-21

RAFT Random Copolymerization of the MPC Monomer and a Hydrophobic Methacrylate Monomer Carried Out in Alcohol at 80° C. or More 4-Cyano-4-[(dodecylsulfanylthiocarbonyl)sulfanyl]pentanoic acid (CTTC) or 4-cyanopentanoic acid dithiobenzoate (CDTB) (used as chain transfer agents) was dissolved in alcohol. After purging with nitrogen for 30 min, 4'-azobis (4-cyanovaleric acid) (ACVA) or 2,2'-azobis(2-methylpropionitrile) (AIBN) (as an initiator) was added to the stirred solution under a flow of nitrogen. The MPC monomer and a hydrophobic methacrylate monomer, for example, n-butyl methacrylate (BMA), 2-ethylhexyl methacrylate (EHMA), or ethyl methacrylate (EMA), were added to the reaction mixture. The reaction mixture was kept at 80° C. or more under nitrogen. After the reaction was completed, the solution was dialyzed using a Spectra/Por 3 tubing (molecular weight cut-off=3.5 kDa) manufactured by Spectrum Laboratories, Inc. The dialysis tubing was placed in the alcohol for 2 days, and then vacuum dried.

$^1$H nuclear magnetic resonance (NMR) spectra were recorded on a JeolJNM-LA400 instrument using $CD_3OD$ as a solvent. The molar ratio of the MPC repeating unit and the hydrophobic unit was calculated.

The molecular weight of the polymer was measured using gel permeation chromatography (GPC). The polymer was dissolved in 1,1,1,3,3,3-hexafluoroisopropanol (HFIP) with 10 mM sodium trifluoroacetate. The GPC measurement was conducted using two Agilent PL HFIP gel columns (250×4.6 mm) at 40° C. (the flow rate, 0.2 mL/min; PDI detector) with an injection volume of 35 μl. The poly[n-butyl methacrylate (BMA)] standard samples (Chromtech Inc.) having a molecular weight range from 1,500 to 800,000 were dissolved in HFIP with 10 mM sodium trifluoroacetate and run through the columns under the same conditions as the polymers and used to determine the peak-average molecular weight ($M_p$) and polydispersity (PDI) of the polymers.

Table 1-2 shows the conditions and results for Samples 1-22.

The molar ratio of total monomers and CTA was used to control the $M_p$ of the copolymers. When the molar ratios ranged from about 35:1 to about 564:1 to 564 (total monomers/CTA), the copolymers synthesized using the RAFT method typically have a PDI of 1.3 or lower. (See Samples 6-10.)

stirred solution under a flow of nitrogen. The hydrophobic methacrylate monomer was added to the reaction mixture. No MPC monomer was added to the reaction mixture. The reaction mixture was kept at 90° C. or above under nitrogen. After the reaction was complete, the solution was poured into a large excess of n-hexane for precipitation of the product, and then vacuum dried.

The molecular weight of the homopolymer was measured using gel permeation chromatography (GPC). The polymer was dissolved in 1,1,1,3,3,3-hexafluoroisopropanol (HFIP) with 10 mM sodium trifluoroacetate. The GPC measurement was conducted using two Agilent PL HFIP gel columns (250×4.6 mm) at 40° C. (the flow rate, 0.2 mL/min; PDI detector) with an injection volume of 35 μl. The poly[n-butyl methacrylate (BMA)] standard samples (Chromtech Inc.) having a molecular weight range from 1,500 to 800,000 were dissolved in HFIP with 10 mM sodium trifluoroacetate and run through the columns under the same conditions as

TABLE 1-2

| No. | Hydrophobic Monomer, Conc. (M) | MPC Conc. (M) | CTA, Conc. (M) | Initiator, Conc. (M) | Solvent | Temp. (° C.) | Reaction Time (Hours) | MPC mol % | $M_p$, PDI |
|---|---|---|---|---|---|---|---|---|---|
| 1 | BMA, 3.95 | 1.69 | CTTC, 0.040 | ACVA, 0.0080 | EtOH | 90 | 18 | 30 | 68k, 1.13 |
| 2 | BMA, 3.95 | 1.69 | CTTC, 0.080 | ACVA, 0.0080 | EtOH | 90 | 18 | 29 | 42k, 1.15 |
| 3 | BMA, 3.95 | 1.69 | CDTB, 0.040 | AIBN, 0.0080 | EtOH | 90 | 18 | 30 | 55k, 1.16 |
| 4 | BMA, 3.95 | 1.69 | CTTC, 0.040 | ACVA, 0.0080 | BuOH | 130 | 4 | 30 | 62k, 1.19 |
| 5 | BMA, 0.395 | 0.169 | CDTB, 0.004 | AIBN, 0.0008 | EtOH | 80 | 48 | 30 | 42k, 1.22 |
| 6 | BMA, 2.82 | 2.82 | CTTC, 0.010 | ACVA, 0.0080 | EtOH | 90 | 18 | 47 | 309k, 1.23 |
| 7 | BMA, 2.82 | 2.82 | CTTC, 0.020 | ACVA, 0.0080 | EtOH | 90 | 18 | 51 | 155k, 1.20 |
| 8 | BMA, 2.82 | 2.82 | CTTC, 0.040 | ACVA, 0.0080 | EtOH | 90 | 18 | 52 | 90k, 1.14 |
| 9 | BMA, 2.82 | 2.82 | CTTC, 0.080 | ACVA, 0.0080 | EtOH | 90 | 18 | 52 | 61k, 1.18 |
| 10 | BMA, 1.13 | 4.51 | CTTC, 0.160 | ACVA, 0.0160 | EtOH | 90 | 18 | 81 | 42k, 1.15 |
| 11 | BMA, 3.95 | 1.69 | CDTB, 0.040 | AIBN, 0.0080 | MeOH | 80 | 18 | 30 | 101k, 1.11 |
| 12 | BMA, 3.95 | 1.69 | CDTB, 0.040 | AIBN, 0.0080 | MeOH | 90 | 18 | 30 | 120k, 1.10 |
| 13 | EHMA, 0.136 | 0.542 | CTTC, 0.005 | ACVA, 0.0011 | EtOH | 90 | 18 | 80 | 74k, 1.17 |
| 14 | EHMA, 0.452 | 0.676 | CTTC, 0.008 | ACVA, 0.0016 | EtOH | 90 | 18 | 56 | 76k, 1.19 |
| 15 | EHMA, 0.904 | 1.352 | CTTC, 0.032 | ACVA, 0.0064 | EtOH | 90 | 18 | 60 | 53k, 1.15 |
| 16 | EHMA, 0.226 | 0.338 | CTTC, 0.004 | ACVA, 0.0016 | BuOH | 120 | 6 | 60 | 50k, 1.23 |
| 17 | EHMA, 2.82 | 2.82 | CTTC, 0.040 | ACVA, 0.0080 | EtOH | 90 | 18 | 50 | 73k, 1.17 |
| 18 | EHMA, 1.13 | 4.51 | CTTC, 0.080 | ACVA, 0.0080 | EtOH | 90 | 18 | 83 | 68k, 1.19 |
| 19 | EMA, 3.95 | 1.69 | CTTC, 0.040 | ACVA, 0.0080 | EtOH | 90 | 18 | 29 | 62k, 1.25 |
| 20 | EMA, 2.82 | 2.82 | CTTC, 0.080 | ACVA, 0.0080 | EtOH | 90 | 18 | 42 | 117k, 1.12 |
| 21 | EMA, 2.82 | 2.82 | CTTC, 0.020 | ACVA, 0.0080 | EtOH | 90 | 18 | 47 | 229k, 1.22 |
| 22 | EMA, 1.13 | 4.51 | CTTC, 0.160 | ACVA, 0.0160 | EtOH | 90 | 18 | 84 | 36k, 1.14 |

Comparative Homopolymer Samples 1.1-1.6.

RAFT Polymerization of a Hydrophobic Methacrylate Monomer in Alcohol without MPC Monomer 4-cyanopentanoic acid dithiobenzoate (CDTB) or 4-cyano-4-[(dodecylsulfanylthiocarbonyl)sulfanyl]pentanoic acid (CTTC) (as chain transfer agents) (CTAs) was dissolved in alcohol. After purging with nitrogen for 30 min, 4'-azobis(4-cyanovaleric acid) (ACVA) or 2,2'-azobis(2-methylpropionitrile) (AIBN) as an initiator was added to the the polymers and used to determine the peak-average molecular weight ($M_p$) and polydispersity (PDI) of the polymers.

Table 1-3 shows the conditions and results for Comparative Samples 1.1-1.6. Without the MPC monomer, the RAFT-polymerization of the hydrophobic methacrylate monomer in alcohol was not as controlled and the PDI was greater than 1.4.

TABLE 1-3

| Comparative Samples | Hydrophobic Methacrylate Monomer, Conc. (M) | CTA, Conc. (M) | Initiator, Conc. (M) | Solvent | Polymerization Temp., Time | Product ($M_p$, PDI) |
|---|---|---|---|---|---|---|
| 1.1 | BMA, 3.95 | CTTC, 0.040 | ACVA, 0.0008 | EtOH | 90° C., 12 h | X |
| 1.2 | BMA, 5.64 | CTTC, 0.040 | ACVA, 0.0008 | EtOH | 90° C., 12 h | X |
| 1.3 | BMA, 5.64 | CDTB, 0.040 | AIBN, 0.0008 | EtOH | 90° C., 12 h | X |
| 1.4 | BMA, 5.64 | CDTB, 0.040 | AIBN, 0.0008 | BuOH | 120° C., 6 h | 24k, 1.42 |
| 1.5 | EHMA, 2.82 | CTTC, 0.040 | ACVA, 0.0008 | EtOH | 90° C., 18 h | X |
| 1.6 | EMA, 2.82 | CTTC, 0.040 | ACVA, 0.0008 | EtOH | 90° C., 18 h | 16k, 1.42 |

"X" in Table 1-3, above, indicates that polymerization did not occur.

Comparative Samples 1.7-1.12.

RAFT Random Copolymerization of the MPC Monomer and a Hydrophobic Methacrylate Monomer in Alcohol at 70° C. or Below 4-cyanopentanoic acid dithiobenzoate (CDTB) or 4-Cyano-4-[(dodecylsulfanylthiocarbonyl)sulfanyl]pentanoic acid (CTTC) (as chain transfer agents) (CTAs) was dissolved in alcohol. After purging with nitrogen for 30 min, 4'-azobis(4-cyanovaleric acid) (ACVA) or 2,2'-azobis(2-methylpropionitrile) (AIBN) (as an initiator) was added to the stirred solution under a flow of nitrogen. The MPC monomer and a hydrophobic monomer were added to the reaction mixture. The reaction mixture was kept at 70° C. or below under nitrogen. After the reaction was complete, the solution was poured into a large excess of n-hexane for precipitation of the product, and then vacuum dried. $^1$H nuclear magnetic resonance (NMR) spectra were recorded on a JeolJNM-LA400 instrument using $CD_3OD$ as a solvent. The molar ratio of the MPC units and the hydrophobic units was calculated.

Table 1-4 shows the conditions and results for Comparative Samples 1.7-1.12. RAFT random copolymerization of the MPC monomer and a hydrophobic monomer was not induced in alcohol when the polymerization temperature was at 70° C. or below.

Laboratories, Inc. The dialysis tubing was placed in phosphate buffered saline (PBS) for 3 days, in distilled water for 2 hours, and in methanol for 2 hours, and then vacuum dried.

$^1$H nuclear magnetic resonance (NMR) spectra were recorded on a JeolJNM-LA400 instrument using $CD_3OD$ as a solvent. The molar ratio of the MPC unit and the hydrophobic unit of the copolymer was calculated.

The molecular weight of the copolymer was measured using gel permeation chromatography (GPC). The copolymer was dissolved in 1,1,1,3,3,3-hexafluoroisopropanol (HFIP) with 10 mM sodium trifluoroacetate. The GPC measurement was conducted using two Agilent PL HFIPgel columns (250×4.6 mm) at 40° C. (the flow rate, 0.2 mL/min) with an injection volume of 35 μl. The poly[n-butyl methacrylate (BMA)] standard samples (Chromtech Inc.) having a molecular weight range from 1,500 to 800,000 were dissolved in HFIP with 10 mM sodium trifluoroacetate and run through the columns under the same conditions as the polymers and used to determine the peak-average molecular weight ($M_p$) and polydispersity (PDI) of phosphorylcholine group-containing copolymer.

Samples 2.1-2.9

Table 2-1 shows that copolymers containing phosphorylcholine groups prepared by the RAFT method and having an

TABLE 1-4

| Comparative Samples | Hydrophobic Monomer Conc. (M) | MPC Monomer Conc. (M) | CTA, Conc. (M) | Initiator, Conc. (M) | Solvent | Polymerization Temp., Time | Product | MPC mol % |
|---|---|---|---|---|---|---|---|---|
| 1.7 | BMA, 0.395 | 0.169 | CDTB, 0.0040 | ACVA, 0.0008 | MeOH | 70° C., 48 h | X | — |
| 1.8 | BMA, 0.395 | 0.169 | CDTB, 0.0020 | ACVA, 0.0008 | MeOH | 70° C., 48 h | X | — |
| 1.9 | BMA, 0.395 | 0.169 | CDTB, 0.0040 | AIBN, 0.0008 | MeOH | 70° C., 48 h | ◯ | 100 |
| 1.10 | BMA, 1.053 | 0.451 | CDTB, 0.0105 | ACVA, 0.0021 | MeOH | 60° C., 33 h | X | — |
| 1.11 | EHMA, 1.352 | 0.902 | CTTC, 0.0320 | ACVA, 0.0064 | EtOH | 70° C., 18 h | X | — |
| 1.12 | EHMA, 1.352 | 0.902 | CTTC, 0.0160 | ACVA, 0.0064 | EtOH | 70° C., 18 h | X | — |

"X" in Table 1-4 indicates that polymerization did not occur.
"◯" in Table 1-4 indicates that polymerization did occur.

Urinary Excretion of Copolymers Containing Phosphorylcholine Groups

Copolymers containing phosphorylcholine groups were sterilized with ethylene oxide gas at 40° C. 100 mg of phosphorylcholine group-containing polymer was dissolved in 1 mL of normal saline. After Sprague Dawley rats were anesthetized by inhalation of 2% isofluorane, 1 mL of the phosphorylcholine group-containing copolymer solution was injected into a tail vein. The animals were kept in metabolic cages. The urine of rats was collected for 1 day after the injection/administration.

The urine was dialyzed using Spectra/Por 3 tubing (molecular weight cut-off=3.5 kDa) manufactured by Spectrum $M_p$ less than 130,000 could penetrate the kidney and were excreted in urine. The $M_p$ and PDI of phosphorylcholine group-containing copolymer were not substantially changed after the urinary excretion. It is known that biocompatible polymers that form biomembrane-like structures can enhance biocompatibility and/or bioabsorbability. Copolymers like those in samples 2.1-2.9 can be beneficial as they are resorbable/bioabsorbable upon introduction into a mammal. In addition, such copolymers, having low $M_p$ and PDI, can be excreted in the urine and do not contain larger sized copolymers that cannot be excreted in the mammal's urine.

TABLE 2-1

| Samples | Polymer | MPC mol % before injection | MPC mol % after excretion | $M_p$, PDI before injection | $M_p$, PDI after excretion |
|---|---|---|---|---|---|
| 2.1 | Poly(MPC-co-BMA) | 30 | 30 | 95k, 1.10 | 93k, 1.11 |
| 2.2 | Poly(MPC-co-BMA) | 30 | 30 | 95k, 1.10 | 100k, 1.09 |
| 2.3 | Poly(MPC-co-BMA) | 29 | 29 | 62k, 1.14 | 68k, 1.11 |
| 2.4 | Poly(MPC-co-BMA) | 29 | 29 | 62k, 1.14 | 62k, 1.10 |
| 2.5 | Poly(MPC-co-BMA) | 30 | 30 | 114k, 1.13 | 119k, 1.10 |
| 2.6 | Poly(MPC-co-EHMA) | 48 | 48 | 91k, 1.18 | 91k, 1.15 |
| 2.7 | Poly(MPC-co-EHMA) | 48 | 48 | 48k, 1.23 | 50k, 1.15 |
| 2.8 | Poly(MPC-co-BMA) | 30 | 30 | 51k, 1.25 | 55k, 1.20 |
| 2.9 | Poly(MPC-co-BMA) | 30 | 30 | 51k, 1.25 | 50k, 1.19 |

Comparative Samples 2.1-2.8 Synthesized with a Conventional Radical Polymerization Method If the phosphorylcholine group-containing copolymer had an $M_p$ more than 130,000, the copolymer could not be excreted in urine. Table 2-2 shows that copolymers having an $M_p$ of more than 130,000 and prepared by a conventional radical polymerization method (without a CTA) underwent a significant decrease in $M_p$ following urinary excretion. Only phosphorylcholine group-containing copolymers with an $M_p$ of less than 130,000 were excreted in the urine, suggesting that the larger sized phosphorylcholine group-containing copolymers (molecular weight greater than 130,000) could not be secreted in the urine and remained in the body.

TABLE 2-2

| Comparative Samples | Polymer | MPC mol % before injection | MPC mol % after excretion | $M_p$, PDI before injection | $M_p$, PDI after excretion |
| --- | --- | --- | --- | --- | --- |
| 2.1 | Poly(MPC-co-BMA) | 80 | 80 | 552k, 1.49 | 120k, 1.24 |
| 2.2 | Poly(MPC-co-EHMA) | 56 | 56 | 141k, 1.17 | 128k, 1.14 |
| 2.3 | Poly(MPC-co-EHMA) | 56 | 56 | 141k, 1.17 | 103k, 1.14 |
| 2.4 | Poly(MPC-co-BMA) | 52 | 52 | 309k, 1.23 | 95k, 1.24 |
| 2.5 | Poly(MPC-co-BMA) | 47 | 47 | 288k, 1.29 | 91k, 1.20 |
| 2.6 | Poly(MPC-co-BMA) | 30 | 30 | 133k, 1.19 | 55k, 1.26 |
| 2.7 | Poly(MPC-co-BMA) | 52 | 52 | 150k, 1.13 | 82k, 1.18 |
| 2.8 | Poly(MPC) | 100 | 100 | 174k, 1.16 | 28k, 1.27 | cantly (below 1.3), indicating that a significant portion of the larger sized phosphorylcholine group-containing copolymer (molecular weight greater than 130,000) was not excreted and, thus, remained in the body. Thus, phosphorylcholine group-containing copolymers synthesized using the conventional radical polymerization method and having a PDI greater than 1.3 represent a wider distribution of variable length copolymers. While the low molecular weight copolymers in such a distribution may penetrate the kidney and pass through the urine, the higher molecule weight copolymers in the distribution are not excreted in the urine and thus remain in the body.

TABLE 2-3

| Comparative Samples | Polymer | MPC mol % before injection | MPC mol % after excretion | $M_p$, PDI before injection | $M_p$, PDI after excretion |
| --- | --- | --- | --- | --- | --- |
| 2.9 | Poly(MPC-co-BMA) | 39 | 39 | 91k, 2.09 | 91k, 1.22 |
| 2.10 | Poly(MPC-co-BMA) | 39 | 39 | 91k, 2.09 | 89k, 1.25 |

Comparative Samples 2.9-2.10 Synthesized with a Conventional Radical Polymerization Method If $M_p$ of phosphorylcholine group-containing copolymer was less than 130,000 and PDI of phosphorylcholine group-containing copolymer was more than 1.3, the molecular weight distribution of phosphorylcholine group-containing copolymer, as reflected in the PDI, changed significantly following urinary excretion. As shown in Table 2-3, for phosphorylcholine group-containing copolymer prepared using a conventional radical polymerization method as disclosed in U.S. Pat. No. 6,214,957 (the contents of which are hereby incorporated by reference in their entirety) with an $M_p$ less than 130,000 and PDI greater than 1.3, the $M_p$ of the phosphorylcholine group-containing copolymer remained relatively unchanged following excretion, but the PDI of the polymers following urinary excretion decreased signifi- Comparative Samples 2.11-2.14

Table 2-4 provides data that suggests phosphorylcholine group-containing copolymer without sufficient hydrophobic units cannot be excreted in the urine. With phosphorylcholine group-containing copolymer with a hydrophobic repeating unit having the formula (III)

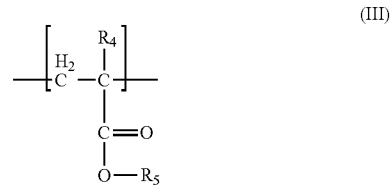

wherein $R^4$ is a hydrogen atom or a methyl group, $R^5$ is an alkyl group having less than 3 carbon atoms, the copolymers underwent a significant decrease in $M_p$ following urinary excretion even if their Mp was less than 130,000 before their administration to a mammal. This suggests that the minimum hydrophobic unit for the urinary excretion of phosphorylcholine group-containing copolymer is $R^5$ having more than 3 carbon atoms

TABLE 2-4

| Comparative Samples | Polymer | MPC mol % before injection | MPC mol % after excretion | $M_p$, PDI before injection | $M_p$, PDI after excretion |
|---|---|---|---|---|---|
| 2.11 | Poly(MPC-co-EMA) | 42 | 42 | 117k, 1.13 | 55k, 1.25 |
| 2.12 | Poly(MPC-co-EMA) | 64 | 64 | 36k, 1.14 | 18k, 1.28 |
| 2.13 | Poly(MPC) | 100 | 100 | 79k, 1.19 | 43k, 1.22 |
| 2.14 | Poly(MPC) | 100 | 100 | 79k, 1.19 | 51k, 1.20 |

Comparative Samples 2.15-2.18.

Phosphorylcholine group-containing copolymer having sufficient hydrophobic units can be excreted in the urine. When the MPC monomer mole fraction of phosphorylcholine group-containing copolymer was more than 80% (Comparative Samples 2.15-2.18), $M_p$ and PDI changed substantially after urinary excretion. Thus, when the MPC monomer mole fraction of phosphorylcholine group-containing copolymer is 80% or less it can be excreted in the urine without a substantial change in $M_p$ or PDI.

TABLE 2-5

| Comparative Samples | Polymer | MPC mol % before injection | MPC mol % after excretion | $M_p$, PDI before injection | $M_p$, PDI after excretion |
|---|---|---|---|---|---|
| 2.15 | Poly(MPC-co-BMA) | 81 | 81 | 39k, 1.14 | 17k, 1.28 |
| 2.16 | Poly(MPC-co-BMA) | 81 | 81 | 39k, 1.14 | 17k, 1.30 |
| 2.17 | Poly(MPC-co-EHMA) | 83 | 83 | 68k, 1.19 | 59k, 1.23 |
| 2.18 | Poly(MPC-co-EHMA) | 83 | 83 | 68k, 1.19 | 46k, 1.21 |

A Polymer Blend

Poly(L-lactic acid) (PLLA; inherent viscosity (i.v.)=1.6) or poly(L-lactide-co-caprolactone; 95-5) (PLCL; i.v.=1.7) were blended with phosphorylcholine group-containing copolymer (Sample 2 in Table 1-2). Six wt % polymer solutions in dichloromethane and methanol (12/1, v/v) were prepared, followed by stirring of the solutions until they became transparent. The solutions were sonicated in a cold bath with ice for 30 min for homogenization. To fabricate cast films, the polymer solutions were cast onto Teflon dishes, and the solvents were dried overnight at room temperature. All samples were dried in vacuo at room temperature for a day, followed by drying in vacuo at 60° C. for 2 days. The samples were then stored in vacuo before use.

The cast films were cut into barbell-shaped films. The breaking strength and Young's modulus of the barbell-shaped cast films were measured with a tensile tester. The crosshead speed was 10 mm/min.

TABLE 3-1

| Blend (PLLA wt/Sample wt) | Breaking Strength (MPa) |
|---|---|
| PLLA | 44.2 ± 2.5 |
| PLLA/Sample 1.2 (99/1) | 55.5 ± 4.2 |

TABLE 3-1-continued

| Blend (PLLA wt/Sample wt) | Breaking Strength (MPa) |
|---|---|
| PLLA/Sample 1.2 (92/8) | 53.1 ± 3.9 |
| PLLA/Sample 1.2 (90/10) | 49.6 ± 2.1 |

TABLE 3-2

| Blend (PLCL wt/Sample wt) | Breaking Strength (MPa) |
|---|---|
| PLCL | 51.3 ± 1.3 |
| PLCL/Sample 1.2 (99/1) | 57.6 ± 2.1 |
| PLCL/Sample 1.2 (92/8) | 50.6 ± 3.5 |
| PLCL/Sample 1.2 (90/10) | 47.1 ± 2.4 |

Blends of bioabsorbable polymers and phosphorylcholine group-containing copolymer having an $M_p$ less than 130,000 and a PDI less than 1.3 had strong mechanical properties higher than or equivalent to bioabsorbable polymers.

Preparation of Phosphorylcholine Group-Containing Copolymer with Differing Concentrations of Alcohol as Polymerization Solvent The copolymerization of MPC and hydrophobic methacrylate monomer did not occur when the alcoholic solvent contained more than 50% of water. The copolymerization occurred up to 30% of water composition in the solvent.

TABLE 4-1

| No. | BMA Conc. (M) | MPC Conc. (M) | CTTC Conc. (M) | ACVA Conc. (M) | Solvent (v/v) | Temperature (° C.) | Reaction Time (Hours) | Copolymerization |
|---|---|---|---|---|---|---|---|---|
| 4.1 | 3.95 | 1.69 | 0.040 | 0.0080 | EtOH/water (90/10) | 110 | 6 | ○ |
| 4.2 | 3.95 | 1.69 | 0.040 | 0.0080 | EtOH/water (70/30) | 110 | 6 | ○ |
| 4.3 | 3.95 | 1.69 | 0.040 | 0.0080 | EtOH/water (50/50) | 110 | 6 | X |

"X" in Table 4-1 indicates that polymerization did not occur.
"○" in Table 4-1 indicates that polymerization did occur.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "containing," "including," "includes," "having," "has," "with," or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g., −1, −1.2, −1.89, −2, −2.5, −3, −10, −20, and −30, etc.

What is claimed is:

1. A method of synthesizing a random copolymer comprising a phosphorylcholine group, said method comprising:
    combining at least one hydrophobic methacrylate monomer and a solvent to produce a microemulsion before preparing a reaction mixture;
    preparing the reaction mixture, wherein said preparing method comprises combining the microemulsion with at least one chain transfer agent (CTA) comprising a thiocarbonylthio group, a 2-methacryloyloxyethyl phosphorylcholine (MPC) monomer, and an initiator and wherein droplets of the hydrophobic methacrylate monomer in the microemulsion are stabilized by the MPC monomer; and
    polymerizing the at least one hydrophobic methacrylate monomer and the MPC monomer at a reaction temperature of 80° C. or above to form the random copolymer,
    wherein the solvent comprises an alcohol having the formula $R^3$—OH, wherein $R^3$ is an alkyl group having 1 to 4 carbon atoms;
    wherein the at least one hydrophobic methacrylate monomer has the following formula:

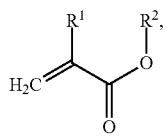

wherein $R^1$ is a hydrogen atom or a methyl group and $R^2$ is an alkyl group having 3 to 8 carbon atoms;
    wherein the random copolymer formed by the polymerization step has a polydispersity index (PDI) of less than about 1.3 and a peak molecular weight ($M_p$) of less than about 130,000, and
    wherein the initiator comprises 2,2'-azobis (2-amidinopropane) dihydrochloride, 4,4'-azobis(4-cyanovaleric acid) (ACVA), 2,2'-azobis (2-(5-methyl-2-imidazoline-2-yl)propane)dihydrochloride, 2,2'-azobis (2-(2-imidazoline-2-yl)propane)dihydrochloride, 2,2'-azobisisobutylamide dihydrate, ammonium persulfate, potassium persulfate, benzoyl peroxide, diisopropyl peroxy dicarbonate, t-butylperoxy-2-ethylhexanoate, t-butyl peroxypivalate, t-butylperoxydiisobutylate, lauroyl peroxide, azobisisobutyronitrile (AIBN), 2,2'-azobis(2,4-dimethylvaleronitrile), t-butyl peroxyneodecanoate, 2,2'-azobis(2-methylpropionamidine) dihydrochloride (AAPH), 1,1'-azobis(cyclohexanecarbonitrile) (ACHN), or a mixture of two or more thereof.

2. The method of claim 1, wherein the CTA comprises a dithioester, a dithiocarbamate, a trithiocarbonate, a xanthate, or a mixture of two or more thereof.

3. The method of claim 1, wherein the initiator comprises azobisisobutyronitrile (AIBN) or 4,4'-azobis(4-cyanovaleric acid) (ACVA).

4. The method of claim 1, wherein the mole ratio of CTA to the initiator is between about 2.5:1 and about 10:1.

5. The method of claim 1, wherein the at least one hydrophobic methacrylate monomer comprises n-butyl methacrylate (BMA), 2-ethylhexyl methacrylate (EHMA), or a mixture of two or more thereof.

6. The method of claim 1, wherein the random copolymer has a PDI of less than about 1.2.

7. The method of claim 1, wherein the random copolymer comprises about 80 mol % or less of a repeating unit comprising a phosphorylcholine group and about 20 mol % or more of a hydrophobic repeating unit.

8. The method of claim 1, wherein the random copolymer has a peak molecular weight ($M_p$) of less than about 120,000.

9. A method of synthesizing a random copolymer comprising a phosphorylcholine group, said method comprising:
    combining at least one hydrophobic methacrylate monomer and a solvent to produce a microemulsion before preparing a reaction mixture;
    preparing the reaction mixture, wherein said preparing method comprises combining the microemulsion with at least one chain transfer agent (CTA) comprising a thiocarbonylthio group, a 2-methacryloyloxyethyl phosphorylcholine (MPC) monomer, and an initiator, and wherein droplets of the hydrophobic methacrylate monomer in the microemulsion are stabilized by the MPC monomer; and
    polymerizing the at least one hydrophobic methacrylate monomer and the MPC monomer at a reaction temperature of 80° C. or above to form the random copolymer,
    wherein the solvent comprises an alcohol having the formula $R^3$—OH, wherein $R^3$ is an alkyl group having 1 to 4 carbon atoms;
    wherein the CTA comprises 4-cyano-4-[(dodecylsulfanylthiocarbonyl)sulfanyl]pentanoic acid (CTTC), 4-Cyanopentanoic acid dithiobenzoate (CDTB), 2-cyano-2-propyl benzodithioate, 2-cyano-2-propyl dodecyl trithiocarbonate, or a mixture of two or more thereof;
    wherein the at least one hydrophobic methacrylate monomer has the following formula:

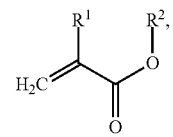

wherein $R^1$ is a hydrogen atom or a methyl group and $R^2$ is an alkyl group having 3 to 8 carbon atoms;

wherein the random copolymer formed by the polymerization step has a polydispersity index (PDI) of less than about 1.2 and a peak molecular weight ($M_p$) of less than about 130,000, and wherein the initiator comprises 2,2'-azobis (2-amidinopropane) dihydrochloride, 4,4'-azobis(4-cyanovaleric acid) (ACVA), 2,2'-azobis (2-(5-methyl-2-imidazoline-2-yl)propane)dihydrochloride, 2,2'-azobis (2-(2-imidazoline-2-yl)propane)dihydrochloride, 2,2'-azobisisobutylamide dihydrate, ammonium persulfate, potassium persulfate, benzoyl peroxide, diisopropyl peroxy dicarbonate, t-butylperoxy-2-ethylhexanoate, t-butyl peroxypivalate, t-butylperoxydiisobutylate, lauroyl peroxide, azobisisobutyronitrile (AIBN), 2,2'-azobis(2,4-dimethylvaleronitrile), t-butyl peroxyneodecanoate, 2,2'-azobis(2-methylpropionamidine) dihydrochloride (AAPH), 1,1'-azobis(cyclohexanecarbonitrile) (ACHN), or a mixture of two or more thereof.

10. The method of claim 9, wherein the at least one hydrophobic methacrylate monomer comprises n-butyl methacrylate (BMA), 2-ethylhexyl methacrylate (EHMA), or a mixture of two or more thereof.

11. The method of claim 9, wherein the initiator comprises azobisisobutyronitrile (AIBN) or 4,4'-azobis(4-cyanovaleric acid) (ACVA).

12. The method of claim 9, wherein the mole ratio of CTA to the initiator is between about 2.5:1 and about 10:1.

13. The method of claim 9, wherein the random copolymer comprises about 80 mol % or less of a repeating unit comprising a phosphorylcholine group and about 20 mol % or more of a hydrophobic repeating unit.

14. The method of claim 9, wherein the molar ratio of the at least one hydrophobic methacrylate monomer to the MPC monomer in the reaction mixture is between about 2.5:1 and about 1:4.

15. The method of claim 9, wherein the reaction temperature is about 90° C. or above.

16. A method of synthesizing a random copolymer comprising a phosphorylcholine group, said method comprising:
combining at least one hydrophobic methacrylate monomer and a solvent to produce a microemulsion before preparing a reaction mixture;
preparing the reaction mixture, wherein said preparing method comprises combining the microemulsion with at least one chain transfer agent (CTA) comprising a thiocarbonylthio group, a 2-methacryloyloxyethyl phosphorylcholine (MPC) monomer, and an initiator, and wherein droplets of the hydrophobic methacrylate monomer in the microemulsion are stabilized by the MPC monomer; and
polymerizing the at least one hydrophobic methacrylate monomer and the MPC monomer at a reaction temperature of 80° C. or above to form the random copolymer,
wherein the solvent comprises an alcohol having the formula $R^3$—OH, wherein $R^3$ is an alkyl group having 1 to 4 carbon atoms;
wherein the CTA comprises 4-cyano-4-[(dodecylsulfanylthiocarbonyl)sulfanyl]pentanoic acid (CTTC), 4-Cyanopentanoic acid dithiobenzoate (CDTB), 2-cyano-2-propyl benzodithioate, 2-cyano-2-propyl dodecyl trithiocarbonate, or a mixture of two or more thereof;
wherein the at least one hydrophobic methacrylate monomer comprises n-butyl methacrylate (BMA), 2-ethylhexyl methacrylate (EHMA), ethyl methacrylate (EMA), or a mixture of two or more thereof;
wherein the random copolymer formed by the polymerization step has a polydispersity index (PDI) of less than about 1.3 and a peak molecular weight ($M_p$) of less than about 130,000, and
wherein the initiator comprises 2,2'-azobis (2-amidinopropane) dihydrochloride, 4,4'-azobis(4-cyanovaleric acid) (ACVA), 2,2'-azobis (2-(5-methyl-2-imidazoline-2-yl)propane)dihydrochloride, 2,2'-azobis (2-(2-imidazoline-2-yl)propane)dihydrochloride, 2,2'-azobisisobutylamide dihydrate, ammonium persulfate, potassium persulfate, benzoyl peroxide, diisopropyl peroxy dicarbonate, t-butylperoxy-2-ethylhexanoate, t-butyl peroxypivalate, t-butylperoxydiisobutylate, lauroyl peroxide, azobisisobutyronitrile (AIBN), 2,2'-azobis(2,4-dimethylvaleronitrile), t-butyl peroxyneodecanoate, 2,2'-azobis(2-methylpropionamidine) dihydrochloride (AAPH), 1,1'-azobis(cyclohexanecarbonitrile) (ACHN), or a mixture of two or more thereof.

* * * * *

UNITED STATES PATENT AND TRADEMARK OFFICE
CERTIFICATE OF CORRECTION

PATENT NO. : 9,546,229 B2  Page 1 of 1
APPLICATION NO. : 13/730434
DATED : January 17, 2017
INVENTOR(S) : Hyungil Kim It is certified that error appears in the above-identified patent and that said Letters Patent is hereby corrected as shown below:

On the Title Page

After item (22), please add:

-- (60) Related U.S. Application Data
Provisional application No. 61/606,003, filed on March 2, 2012. --

Signed and Sealed this
Twenty-eighth Day of March, 2017

Michelle K. Lee
*Director of the United States Patent and Trademark Office*